United States Patent [19]

Marzoni et al.

[11] Patent Number: 4,713,385

[45] Date of Patent: * Dec. 15, 1987

[54] ALKOXY AND DIALKOXYALKYL ESTERS OF DIHYDROLYSERGIC ACID AND RELATED COMPOUNDS USEFUL AS 5HT RECEPTOR ANTAGONISTS

[75] Inventors: Gifford P. Marzoni; William L. Garbrecht, both of Indianapolis, Ind.

[73] Assignee: Eli Lilly and Company, Indianapolis, Ind.

[*] Notice: The portion of the term of this patent subsequent to Jan. 7, 2003 has been disclaimed.

[21] Appl. No.: 782,341

[22] Filed: Oct. 1, 1985

[51] Int. Cl.$^4$ .................... A61K 31/48; C07D 457/04
[52] U.S. Cl. ........................................ 514/288; 546/69
[58] Field of Search ............................. 546/67, 68, 69; 514/288

[56] References Cited

U.S. PATENT DOCUMENTS

| | | | |
|---|---|---|---|
| 3,113,133 | 12/1963 | Hofmann et al. | 260/285.5 |
| 3,183,234 | 5/1965 | Garbrecht et al. | 260/285.5 |
| 3,228,941 | 1/1966 | Bernardi et al. | 260/285.5 |
| 3,228,943 | 1/1966 | Bernardi et al. | 546/68 |
| 3,249,617 | 5/1966 | Hofmann et al. | 260/285.5 |
| 3,580,916 | 5/1971 | Garbrecht | 260/285.5 |
| 4,230,859 | 10/1980 | Rucman | 546/69 |
| 4,563,461 | 1/1986 | Cohen et al. | 514/288 |

FOREIGN PATENT DOCUMENTS 122044 10/1984 European Pat. Off. .

OTHER PUBLICATIONS

Cohen et al., *J.P.E.T.*, 227, 327 (1983).
Cohen et al., ibid, 232, 770 (1984).
Lemberger et al., *Life Sci.*, 35, 71 (1984).
Cohen et al., *Drug Dev. Res.*, 5, 313 (1985).
Hingten et al., Abstract 37.4, *Soc. for Neurosci.* (13th Annual Meeting, Nov., 1983).

*Primary Examiner*—Donald G. Daus
*Assistant Examiner*—Cecilia Shen
*Attorney, Agent, or Firm*—Bruce J. Barclay; Leroy Whitaker

[57] ABSTRACT

Alkoxy or dialkoxyalkyl esters of 1-substituted-6-$C_{1-4}$ straight chain alkyl (or allyl)ergoline-8$\beta$-carboxylic acid, useful as 5HT receptor antagonists.

18 Claims, No Drawings

ALKOXY AND DIALKOXYALKYL ESTERS OF DIHYDROLYSERGIC ACID AND RELATED COMPOUNDS USEFUL AS 5HT RECEPTOR ANTAGONISTS

BACKGROUND OF THE INVENTION

Garbrecht, U.S. Pat. No. 3,580,916, discloses a group of lysergic (I) and 9,10-dihydrolysergic acid (II) esters formed with various open chain and cyclic diols. The following structures summarize the disclosure in Garbrecht.

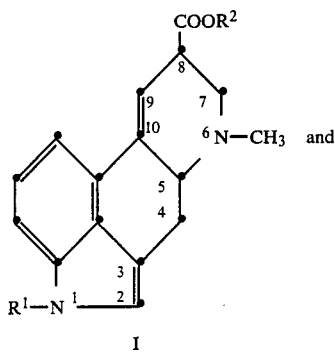

I

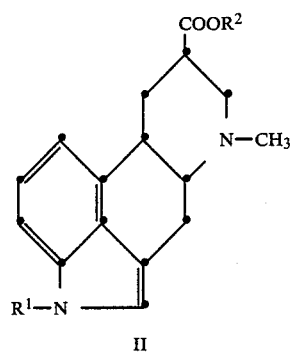

II wherein $R^1$ is H, $C_{1-3}$ alkyl, allyl or benzyl and $R^2$ is $C_2$-$C_8$ monohydroxyalkyl, $C_{2-8}$ dihydroxyalkyl or $C_{5-11}$ monohydroxycycloalkyl having from 5-8 ring carbons. The compounds are useful as serotonin antagonists, the patent stating that "In animals, the compounds act as neurosedatives . . . and are therefore useful in calming . . . animals". The use of compounds according to II, wherein $R^2$ is mono or dihydroxyalkyl, in migraine and other disease states characterized by an excess of peripheral 5HT, is disclosed in EPO No. 122,044 published 10-17-84.

The interest in the Garbrecht compounds has been intensified by the finding that they had excellent peripheral serotonin antagonist activity against $5HT_2$ receptors and did not interact, either as agonists or antagonists, with other receptors, particularly alpha$_1$ receptors.

The most active peripheral serotonin antagonist from Garbrecht was the compound 1-isopropyl-6-methyl-8β-(1-methyl-2-hydroxy)propoxycarbonyl-5R-ergoline (II in which $R^1$ is isopropyl and $R^2$ is 1-methyl-2-hydroxypropyl). In the above name, 5R refers to the beta orientation of the C-5 hydrogen. The C-10 hydrogen is alpha—10R, and the beta orientation at C-8 is the same as in either lysergic or 9,10-dihydrolysergic acid—8R. Both of these acids have a 6-methyl group. An alternate name for the Garbrecht compound is 1-isopropyl-9,10-dihydrolysergic acid 1-methyl-2-hydroxypropyl ester. Cohen et al. *J.P.E.T.*, 227, 327 (1983) (Cohen I) reported that the above compound, given the code number LY53857, was a potent antagonist of vascular contraction to serotonin, which effect is mediated by $5HT_2$ receptors. The compound had minimal affinity for vascular alpha adrenergic, dopaminergic and histaminergic receptors ($K_{dissoc.} \cong 10^{-10}$ vs$\cong 10^{-5}$). Other papers on the pharmacology of LY53857 include Cohen et al., *J.P.E.T.*, 232, 770 (1985) (Cohen III), Harriet Lemberger et al., *Life Sciences*, 35, 71 (1984), Cohen *Drug Development Res.*, 5, 313 (1985), (Cohen IV). Cohen and Fuller, EPO No. 122,044 published 10-17-84, covers the use of hydroxyalkyl esters of 1-alkyl 9,10-dihydrolysergic acid as peripheral $5HT_2$ receptor antagonists.

Four additional examples of ergolines with a substituent on the indole nitrogen are: U.S. Pat. No. 3,113,133, Hofmann et al., which discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofmann et al., which covers (indole) N-alkyl or allyl lysergic acids, useful as intermediates.

U.S. Pat. No. 3,228,941, Bernardi et al., which discloses and claims a group of (indole) N-methylergolines—amides, hydroxamides and amidines. The compounds are alleged to have oxytoxic, adrenolytic, hypotensive, sedative and antienteraminic action.

U.S. Pat. No. 4,230,859 to Rucman which discloses dihydrolysergic acid carrying a $C_{1-5}$ alkyl group on the indole nitrogen, useful as intermediates.

Finally, ergolines actually used in the treatment of migraine include the amides: ergotamine, methysergide and ergonovine.

None of the above references indicate that an alkoxy or dialkoxyalkyl ester of an N-alkylated dihydrolysergic acid would have peripheral serotonin antagonist properties.

SUMMARY OF THE INVENTION

This invention provides ergolines of the formula:

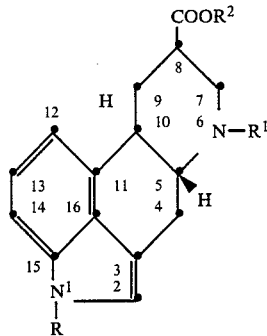

wherein R is primary or secondary $C_{1-8}$ alkyl, $C_{2-4}$ alkenyl-$CH_2$, $C_{3-8}$ cycloalkyl or $C_{3-6}$ cycloalkyl substituted $C_{1-5}$ primary or secondary alkyl, the total number of carbon atoms in R not to exceed 8; $R^1$ is allyl, H or $C_{1-4}$ straight-chain alkyl; i.e., methyl, ethyl, n-butyl, or n-propyl, and $R^2$ is a primary or secondary $C_{1-3}$ alkoxy $C_{2-6}$-alkyl or di($C_{1-3}$ alkoxy)$C_{2-6}$ alkyl; and pharmaceutically acceptable acid addition salts thereof. Compounds according to III, wherein $R^1$ is other than H, are central or peripheral serotonin $5HT_2$ receptor antagonists lacking interaction at 5HT blocking doses with other receptors. Compounds wherein $R^1$ is H are primarily intermediates.

Groups which R represents include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl, isoamyl, 2-methylhexyl, 3-methylhexyl, 4-methylhexyl(isohexyl), 2-hexyl, 3-hexyl, n-heptyl, 2-heptyl, 3-heptyl, 4-heptyl, n-octyl, 2-octyl, 3-octyl, 4-octyl, isooctyl, 2-methylheptyl, 3-methyl-2-heptyl, and the like. Illustrative of the groups which $R^2$ represents include 2-methoxyethyl, 3-methoxypropyl, 2-methoxy-2-methyethyl, 4-methoxybutyl, 5-methoxypentyl, 6-methoxyhexyl, 5-ethoxy-1-methylpentyl 2-n-propoxy-1-methylpropyl, 2-ethoxymethylpropyl, 1-ethoxymethyl-2-ethoxyethyl, 2-ethoxyethyl-4-ethoxybutyl and the like.

Compounds according to the above formula are named as ergoline derivatives in which the trans(−) or 5R,10R configuration of the bridgehead hydrogens is specified (The same configuration as in the naturally-occurring 9,10-dihydro ergot alkaloids). In U.S. Pat. No. 3,580,916, a different naming system is used; the basic ring system is named as a 6aR,10aR-4,6,6a,7,8,9,10,10a-octahydroindolo[4,3-f,g]quinoline. Illustratively, by the alternate naming system 9,10-dihydrolysergic acid becomes 6aR,10aR-7-methyl-4,6,6a,7,8,9,10,10a-octahydroindolo[4,3-f,g]quinoline-9β-carboxylic acid. Another equally valid name for 9,10-dihydrolysergic acid is 6-methyl-8β-carboxyergoline. We prefer to use the trivial name "ergoline" with the numbering system specified in III above for compounds in which $R^1$ is other than methyl and the 9,10-dihydrolysergic acid nomenclature for 6-methyl derivatives.

In addition, in 9,10-dihydrolysergic acid, the C-8 carboxyl is beta or R. Thus, again using the ergoline naming system, derivatives of 9,10-dihydrolysergic acid become derivatives of 5R,8R,10R (or 5β,8β,10α) 6-methylergoline-8β-carboxylic acid.

While the configuration at asymmetric carbons 5,8 and 10 in formula III is set (5β,8β and 10α), the alkoxy or dialkoxyalkyl ester group may contain additional asymmetric carbons. For example, 1-methyl-2-methoxyethanol exists as a racemate containing two enantiomers or stereoisomers. With 1-methyl-2-methoxymethyl-3-methoxypropanol, both carbons 1 and 2 of the alkyl chain are asymmetric and the compound exists as two racemates, each containing 2 enantiomers.

This invention contemplates the use of all such optically active or racemic forms as peripheral serotonin antagonists.

Pharmaceutically-acceptable acid addition salts of the compounds of formula III include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds of this invention include:
1-methyl-6-ethyl-8β-(2-methoxyethyloxycarbonyl)ergoline hydrochloride
1-n-propyl-6-allyl-8β-(3-ethoxypropyloxycarbonyl)ergoline sulfate
4-methoxybutyl 1-methyl-9,10-dihydrolysergate phosphate
1-isopropyl-6-n-propyl-8β-(2-n-propoxypropyloxycarbonyl)ergoline hydrobromide
1-methoxyethyl-3-methoxypropyl-1-n-octyl-9,10-dihydrolysergate
1-allyl-6-ethyl-8β-(4-ethoxyhexyloxycarbonyl)ergoline tartrate and the like.

The preparation of compounds represented by formula III above is the general method of U.S. Pat. No. 3,580,916. According to this procedure, dihydrolysergic acid is first alkylated on the indole nitrogen using standard procedures—base plus an aliphatic halide. Liquid ammonia is a convenient solvent with sodamide as the base and an alkyl, cycloalkyl, or cycloalkyl substituted $C_{1-5}$ alkyl iodide or an alkenyl chloride or bromide as the alkylating agent. (See also U.S. Pat. No. 3,183,234 Garbrecht and Lin, which contains general directions and a specific example of the above alkylation procedure).

Alternatively, the process described in the copending application of Marzoni Ser. No. 782,339 filed this even date, can be used whereby an aryl sulfonate of the formula R—O—SO$_2$-phenyl-Y wherein Y is H, Br, NO$_2$ or CH$_3$ is used in the presence of an alkali metal hydroxide, conveniently sodium hydroxide, in an aprotic solvent such as DMSO.

With the indole nitrogen substituent in place, if 1-R-9,10-dihydrolysergic acid ($R^1$ is methyl) is the starting material, the next step in the synthetic procedure is esterification. This procedure requires relatively mild reaction conditions according to U.S. Pat. No. 3,580,916. The reaction is, however, an otherwise standard acid-catalyzed esterification. The free acid and the alkoxy or dialkoxyalkanol are the reactants and a convenient work-up of the esterification mixture involves partitioning between water and a water-immiscible solvent; (CH$_2$Cl)$_2$ for example.

If the final product is not a 9,10-dihydrolysergic acid ester (i.e.; not a 1-R-6-methylergoline-8β-carboxylic acid ester), but is a 6-ethyl, 6-n-propyl, 6-n-butyl, 6-allyl or the like derivative, the removal of the 6-methyl group must take place prior to the final esterification with an alkoxy or dialkoxyalkanol. In this procedure, we prefer to use a lower alkyl ester of a 1-R-9,10-dihydrolysergic acid as a starting material. Replacement of the 6-methyl group with ethyl, n-propyl, allyl, n-butyl, can be carried out by the procedure of Kornfeld and Bach, U.S. Pat. No. 4,166,182, whereby the 6-methyl group is reacted with cyanogen bromide to form an N-cyano derivative. The cyano group is then removed by hydrogenation using zinc dust and hydrochloric acid or preferably, with base in ethylene glycol or other suitable solvents. This latter procedure yields a product containing a free carboxyl at C-8 since the hydrolysis procedure also saponifies the lower alkyl ester group.

Next, reesterification with the desired $R^2OH$ (alkoxy or dialkoxyalkanol) takes place followed by alkylation or allylation at N-6 using an allyl chloride or alkyl iodide in the presence of base, conveniently in DMF solution.

This procedure is graphically illustrated in Reaction Scheme 1 below.

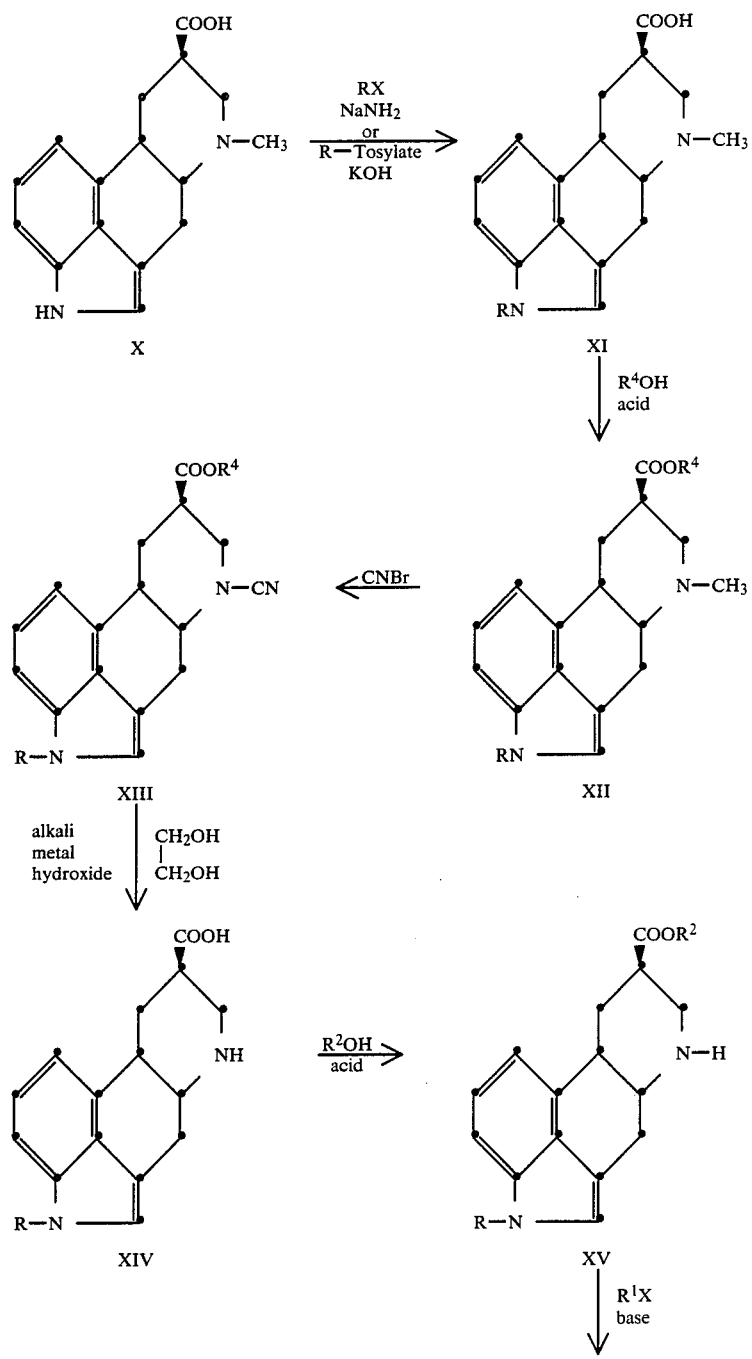

Reaction Scheme 1

Reaction Scheme 1
-continued

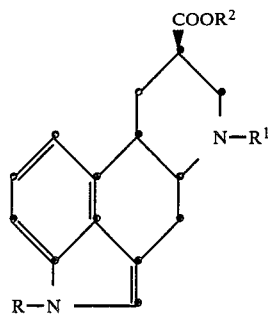

III

More specifically, in the above Reaction Scheme, 9,10-dihydrolysergic acid (X) may be alkylated on the indole nitrogen with an alkyl ($C_{1-8}$ alkyl) halide a $C_{2-4}$ alkenyl-$CH_2$ halide, a $C_{3-6}$ cycloalkyl halide or a $C_{3-6}$ cycloalkyl-$C_{1-5}$ alkyl halide, (RX) using sodamide to create the reactive anion. Preferably, however, a tosylate (R—O—$SO_2$-Tolyl) is employed in the presence of KOH in an aprotic solvent since this latter procedure is more generally applicable than the use of the halide, RX. The product (XI) is then esterified with a lower alkanol $R^4OH$ (a $C_{1-2}$ alkanol preferably) to yield the 1-R alkylated ester (XII). This ester is then reacted with CNBr by standard procedures to replace the methyl group with an N-cyano derivative (XIII). Removal of the cyano group under the preferred basic conditions yields a 1-substituted-9,10-dihydro-6-desmethyllysergic acid (XIV), since the basic conditions also saponifies the C-8 lower alkyl ester group. Next, the 1-R-6-desmethyl-dihydrolysergic acid is re-esterified with a desired alkoxy or dialkoxyalkanol to yield the 6-desmethyl ester (XV). The piperidine ring nitrogen (N-6) is then realkylated with a $C_{1-4}$ alkyl or allyl halide and base under standard conditions to yield the compounds of this invention (III).

It might seem redundant to realkylate at N-6 with a methyl group since that group is present in the 9,10-dihydrolysergic acid starting material. However, the process would enable one to insert a "tagged" ($C^{14}$ or $H^3$) methyl group for metabolic studies.

Although the above reaction sequence has been illustrated with reference to preparing alkoxy- or dialkoxyalkyl esters, it is apparent that the procedure is readily adaptable to the provision of 1,6-dialkyl ergoline carboxylic acid esters formed with open chain diols or keto alkanols of the formula $R^6$—$CHR^5OH$ wherein $R^5$ is H or $CH_3$ and $R^6$ is hydroxy $C_{1-3}$ alkyl or keto $C_{1-3}$ alkyl. Such process in all its ramifications is disclosed in the copending application of Whitten et al Ser. No. 782,337 filed this even date.

The following examples illustrate the preparation of compounds according to III above.

EXAMPLE 1

Preparation of 2-Methoxyethyl 1-Isopropyl-9,10-dihydrolysergate

A reaction mixture, prepared from 2 g of 1-isopropyl-9,10-dihydrolysergic acid, 2 g of p-toluene sulfonic acid and 20 ml of ethylene glycol monomethyl ether (2-methoxyethanol), was heated to 70°-80° C. overnight. TLC ($SiO_2$, $CHCl_3$/MeOH/HOAc, 18:6:1) indicated that reaction was complete. 50 ml of water were added followed by 28% aqueous ammonium hydroxide to pH≅10. The aqueous layer was extracted with two 50 ml portions of ethyl acetate. TLC indicated none of the desired product was in the aqueous layer which was therefore discarded. The organic extracts were dried and the solvent evaporated therefrom; yield of free base of 2-methoxyethyl 1-isopropyl-9,10-dihydrolysergate thus prepared=2.59 g.

The free base was converted to the maleate salt by dissolving the base in a solution of 0.86 g of maleic acid in 15 ml of methanol. 200 ml of ether were added. Crystals began to form and the crystallization mixture was chilled overnight. The crystals were separated by filtration; yield of maleate salt=2.08 g. The crystalline salt was dissolved in methanol, the solution decolorized and ether added to induce crystallization; yield=1.47 g of 94.2% purity by HPLC. The crystals were then treated with 150 ml hot toluene and the toluene solution filtered. Crystals formed in the filtrate on cooling; yield=1.32 g 96.3% pure by HPLC assay. A second recrystallization from hot toluene gave 1.21 g of 2-mathoxyethyl 1-isopropyl-9,10-dihydrolysergate, 96.5% pure by HPLC.

Analysis: Calc.: C, 64.18; H, 7.04; N, 5.76; Found: C, 64.00; H, 6.96; N, 5.62.

EXAMPLE 2

Preparation of 3-Methoxypropyl 1-isopropyl-9,10-dihydrolysergate

Following the procedure of Example 1 3-methoxypropanol was reacted with 1-isopropyl-9,10-dihydrolysergic acid in the presence of p-toluenesulfonic acid. The reaction mixture was worked-up and the ester isolated by the procedure of Example 1; yield=2.46 g. The maleate salt was prepared as in Example 1. Addition of ether to the solution gave a mixture of gum and crystals. The supernate containing the crystals was filtered; the residual gum was eventually discarded after no further crystalline material could be obtained therefrom. The filter cake was purified by preparative HPLC (C-18, 1:1 acetonitrite/0.1 M aqueous ammonium acetate, 150 ml/min). The acetonitrile layers from cuts 9–16 were combined and the volatile constituents removed in vacuo. The resulting aqueous layer was extracted with ($CH_2Cl)_2$, and the organic extract evaporated to dryness to yield 1.09 g of free base (from 2.0 g of starting acid, HPLC converted maleate salt back to free base). The maleate salt was formed again in methanol and ether added to induce crystallization. Yield of 3- methoxypropyl 1-isopropyl-9,10-dihydrolysergate maleate thus prepared was 1.08 g; 99.8% pure; molecular ion at 384.

Analysis: Calc.: C, 64.78; H, 7.25; N, 5.60; Found: C, 64.59; H, 7.00; N, 5.79.

EXAMPLE 3

Preparation of 3-Ethoxypropyl 1-Isopropyl-9,10-dihydrolysergate

Following the procedure of Example 1, 2 g of 1-isopropyl-9,10-dihydrolysergic acid was esterified with 3-ethoxypropanol in the presence of p-toluenesulfonic acid. The free base thus prepared was converted to the maleate salt using the procedure of that Example. Addition of ether to the methanolic salt solution gave crystals which were separated by filtration; yield=1.64 g; 90.3% purity. The crystals were dissolved in methanol and the methanol solution decolorized. Attempted recrystallization from toluene and ethyl acetate gave no increase in purity. Preparative HPLC as in Example 2 gave 0.81 g of free base which was reconverted to the maleate salt. Addition of ether did not give crystals. The solvents were removed and the maleate recrystallized from ethyl acetate/ether; yield of 3-ethoxypropyl 1-isopropyl-9,10-dihydrolysergate maleate=0.81 g; 97.1% pure. Molecular ion at 398.

Analysis: Calc.: C, 65.35; H, 7.44; N, 5.44; Found: C, 65.35; H, 7.21; N, 5.28.

EXAMPLE 4

Preparation of 2-Methoxy-1-methylethyl 1-isopropyl-9,10-dihydrolysergate

Following the procedure of Example 1, 2.0 g of 1-isopropyl-9,10-dihydro-lysergic acid was reacted with an excess of 2-methoxy-1-methylethanol in the presence of p-toluenesulfonic acid. The free base was recovered by procedure of Example 1 and then converted to the maleate salt in methanol. Addition of ether caused crystals of the maleate salt to form. The solution was chilled overnight and then filtered. 1.50 g of maleate was recovered. The solid residue recovered from the organic layer was about 80% pure, and was therefore subjected to preparative HPLC as in Examples 2 and 3. 0.64 g of free base were recovered and were converted to the maleate salt as before. 0.66 g of 3-methoxy-1-methyl 1-isopropyl-9,10-dihydrolysergate maleate thus purified were obtained; purity was 97.3%; molecular ion at 384.

Analysis: Calc.: C, 64.78; H, 7.25; N, 5.60; Found: C, 64.57; H, 7.25; N, 5.37.

EXAMPLE 5

Preparation of 2-Ethoxyethyl 1-Isopropyl-9,10-dihydrolysergate

Following the procedure of Example 1, 2.0 g of 1-isopropyl-9,10-dihydrolysergic acid were esterified with an excess of 2-ethoxyethanol in the presence of p-toluenesulfonic acid. The free base was isolated by the procedure of Example 1 and converted to the maleate salt in methanol as in Example 1. Slow addition of ether to the methanolic solution of the salt produced crystals which were separated by filtration; wt=2.2 g. The filter cake was dissolved in methanol and the methanol solution decolorized. Addition of ether to the filtered decolorization solution gave 1.73 g of 97.8% pure 2-ethoxyethyl 1-isopropyl-9,10-dihydrolysergate maleate. Two crystallization from ethyl acetate/ether gave 1.45 g of maleate which was subjected to preparative HPLC as in Example 1. The acetonitrile solution from the HPLC was partially evaporated, extracted with $(CH_2Cl)_2$. The extract was dried and the solvent evaporated. The 1.18 g residue thus obtained was converted to the maleate salt as before; wt=1.12 g; 99.2% pure. Molecular ion at 384.

Analysis: Calc.: C, 64.78; H, 7.25; N, 5.60; Found: C, 64.55; H, 6.96; N, 5.61.

EXAMPLE 6

Preparation of 1-Ethoxymethyl-2-ethoxyethyl 1-Isopropyl-9,10-dihydrolysergate

Following the procedure of Example 1, 2 g of 1-isopropyl-9,10-dihydrolysergic acid was reacted with an excess of 1,3-diethoxy-2-propanol (1-ethoxymethyl-2-ethoxyethanol) in the presence of p-toluenesulfonic acid. The reaction mixture was worked up and the free base of 1-ethoxymethyl-2-ethoxyethyl 1-isopropyl-9,10-dihydrolyserate formed in the esterfication reaction, isolated by the procedure of Example 1, was converted to the maleate salt in ethyl acetate. Addition of ether resulted in a gum in which on chilling overnight crystals could be seen. This product was further purified by preparative HPLC as in Example 2. The free base thus obtained (wt=0.9 g) was converted to the maleate salt in methanol. Addition of ether produced crystals of the maleate which were collected by filtration; wt=0.92, 99.2% pure by HPLC assay; MP=123°-7° C.; molecular ion at 442.

Analysis: Calc.: C, 64.50; H, 7.58; N, 5.01; Found: C, 64.28; H, 7.75; N, 4.86.

This invention also provides novel methods whereby 5HT receptors are blocked. Such methods are potentially useful in treating disease states in which an excess of circulating serotonin is a major contributing cause. These disease states include hypertension, anorexia nervosa, depression, mania, thrombosis, carcinoid syndrome, migraine and vasospasm. The compounds according to III above show relatively slight affinity for other receptors, $\alpha_1$, $\alpha_2$, $\beta$, histamine, carbachol etc. and thus are highly selective in their action. Formulations in which a compound of this invention is an active ingredient also form another aspect of this invention.

In order to demonstrate that compounds according to formula III have an extremely high affinity for $5HT_2$ receptors, apparent dissociation constants ($K_B$) as a measure of affinity for $5HT_2$ receptors, expressed as the negative logarithm, have been determined according to the following protocol.

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% $CO_2$. An initial optimum resting force of 1 and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.* 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the $ED_{50}$ of the agonist in the presence of the antagonist divided by the control $ED_{50}$. These results are then expressed as the negative logarithm of $K_B$. The $-\log K_B$ values obtained for compounds of this invention are given below in Table 1.

TABLE 1

Apparent Dissociation Constants for $5HT_2$ receptors determined in the rat jugular vein.

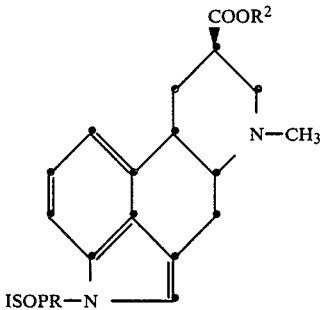

| Compound $R^2$ | salt | $5HT_2$ $-\log K_b \pm$ S.E. |
|---|---|---|
| $CH_2-CH_2-O-CH_3$ | maleate | 8.92 ± 0.±0 (3) |
| $CH_2-CH_2-CH_2-O-CH_3$ | maleate | 8.97 ± 0.12 (3) |
| $CH_2-CH_2-CH_2-O-C_2H_5$ | maleate | 8.88 ± 0.25 (3) |
| $CH_2-CH_2-O-C_2H_5$ | maleate | 8.47 ± 0.12 (4) |
| $C(CH_2-O-C_2H_5)_2$ | maleate | 8.19 ± 0.15 (3) |
| $CH(CH_3)-CH_2-O-CH_3$ | maleate | 9.18 ± 0.26 (4) |

In mammals, hypertension may be mediated through $5HT_2$ receptors. Thus, compounds of formula III would be expected to lower blood pressure in humans as does ketanserin, another $5HT_2$ blocker, but without the side effects attributable to alpha adrenergic receptor blockade of ketanserin.

In carrying out our novel therapeutic process, a pharmaceutically-acceptable salt of a drug according to formula III above formed with a non-toxic acid is administered orally or parenterally to a mammal with an excess of circulatory serotonin in which mammal it is desirable to block $5HT_2$ receptors in order to alleviate symptoms attributable to excessive serotonin levels such as high blood pressure and migraine. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1–10 mg/kg have been found to be effective in blocking $5HT_2$ receptors. Thus, the oral dosage would be administered 2–4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A compound of the formula:

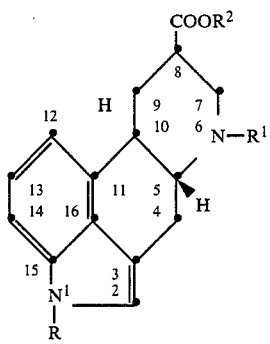

wherein R is primary or secondary $C_{1-8}$ alkyl, $C_{2-4}$ alkenyl-$CH_2$, $C_{3-8}$ cycloalkyl or $C_{3-6}$ cycloalkyl substituted $C_{1-5}$ primary or secondary alkyl, the total number of carbon atoms in R not to exceed 8; $R^1$ is allyl, H or $C_{1-4}$ straight-chain alkyl; and $R^2$ is a primary or secondary $C_{1-3}$ alkoxy $C_{2-6}$-alkyl or di($C_{1-3}$ alkoxy)$C_{2-6}$ alkyl; and pharmaceutically-acceptable salts thereof.

2. A compound according to claim 1 in which R is isopropyl.

3. A compound according to claim 1 in which $R^1$ is H.

4. A compound according to claim 1 in which $R^1$ is $C_{1-4}$ straight chain alkyl.

5. A compound according to claim 1 in which $R^2$ is 2-methoxyethyl.

6. A compound according to claim 1 in which $R^2$ is 3-ethoxypropyl.

7. A compound according to claim 1, said compound being 2-methoxyethyl 1-isopropyl-9,10-dihydrolysergate.

8. A compound according to claim 1, said compound being 3-ethoxypropyl 1-isopropyl-9,10-dihydrolysergate.

9. A compound according to claim 1, said compound being 1-ethoxymethyl-2-ethoxyethyl 1-isopropyl-9,10-dihydrolysergate.

10. A compound according to claim 1, said compound being 2-methoxy-1-methylethyl 1-isopropyl-9,10-dihydrolysergate.

11. A method of blocking $5HT_2$ receptors which comprises administering to a mammal having an excess of serotonin centrally or peripherally an $5HT_2$ blocking dose of a compound according to claim 4.

12. A method of treating hypertension which comprises administering to a hypertensive mammal, a hypotensive dose of a compound according to claim 4.

13. A method of treating migraine which comprises administering to a mammal suffering from migraine, a migraine relieving dose of a compound according to claim 4.

14. A method of treating vasospasm which comprises administering to a mammal experiencing vasospasm, a vasospasm relieving dose of a compound according to claim 4.

15. A process according to claim 11 in which 2-methoxyethyl 1-isopropyl-9,10-dihydrolysergate is the drug employed.

16. A process according to claim 11 in which 3-ethoxypropyl 1-isopropyl-9,10-dihydrolysergate is the drug employed.

17. A process according to claim 12 in which 2-methoxyethyl 1-isopropyl-9,10-dihydrolysergate is the drug employed.

18. A process according to claim 12 in which 3-ethoxypropyl 1-isopropyl-9,10-dihydrolysergate is the drug employed.

* * * * *